(12) United States Patent
Kawata et al.

(10) Patent No.: US 12,290,511 B2
(45) Date of Patent: *May 6, 2025

(54) PHARMACEUTICAL PREPARATION CONTAINING PYRIDYL AMINOACETIC ACID COMPOUND

(71) Applicant: Santen Pharmaceutical Co., Ltd., Osaka (JP)

(72) Inventors: Hisashi Kawata, Osaka (JP); Noriko Kawabata, Osaka (JP); Naveed Shams, Emeryville, CA (US)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/314,909

(22) Filed: May 10, 2023

(65) Prior Publication Data

US 2023/0277515 A1  Sep. 7, 2023

Related U.S. Application Data

(63) Continuation of application No. 16/957,749, filed as application No. PCT/JP2018/048228 on Dec. 27, 2018, now Pat. No. 11,666,563.

(60) Provisional application No. 62/611,017, filed on Dec. 28, 2017.

(51) Int. Cl.
*A61K 31/444* (2006.01)
*A61K 9/00* (2006.01)
*A61K 31/5575* (2006.01)

(52) U.S. Cl.
CPC .......... *A61K 31/444* (2013.01); *A61K 9/0048* (2013.01); *A61K 31/5575* (2013.01)

(58) Field of Classification Search
CPC ..... A61K 31/444; A61K 31/5575; A61K 9/00
USPC ....................................................... 514/333
See application file for complete search history.

(56) References Cited

U.S. PATENT DOCUMENTS

| | | | |
|---|---|---|---|
| 8,685,986 B2 | 4/2014 | Hagihara et al. | |
| 9,339,496 B2 | 5/2016 | Kirihara et al. | |
| 9,415,038 B2 | 8/2016 | Shams et al. | |
| 11,666,563 B2 * | 6/2023 | Kawata | A61P 27/06 514/333 |
| 2011/0054172 A1 | 3/2011 | Iwamura et al. | |
| 2012/0190852 A1 | 7/2012 | Hagihara et al. | |
| 2014/0018350 A1 | 1/2014 | Kirihara et al. | |
| 2014/0018396 A1 | 1/2014 | Kirihara et al. | |
| 2015/0196541 A1 | 7/2015 | Shams et al. | |
| 2016/0317512 A1 | 11/2016 | Endo | |
| 2016/0317664 A1 | 11/2016 | Endo | |
| 2016/0324838 A1 | 11/2016 | Shams et al. | |
| 2018/0169079 A1 | 6/2018 | Shams et al. | |
| 2018/0185489 A1 | 7/2018 | Miyazaki et al. | |
| 2018/0200239 A1 | 7/2018 | Kirihara et al. | |
| 2019/0105310 A1 | 4/2019 | Shams et al. | |
| 2020/0345713 A1 | 11/2020 | Kawata et al. | |

FOREIGN PATENT DOCUMENTS

| | | |
|---|---|---|
| WO | 2015105134 A1 | 7/2015 |
| WO | 2015105135 A1 | 7/2015 |
| WO | 2015105144 A1 | 7/2015 |
| WO | 2017002941 A1 | 1/2017 |
| WO | 2017006985 A1 | 1/2017 |

OTHER PUBLICATIONS

Aihara, et al., "Ocular Hypotensive Effect of Tafluprost in Latanoprost Low-Responder Monkeys", General Lectures, Japanese Ophthalmological Society, vol. 113, No. 01-017, 2009, with an English translation. (5 pages).

Extended European Search Report issued on Aug. 18, 2021, in the corresponding European Patent Application No. 18896002.5. (13 pages).

Ikeda, et al., "Latanoprost Nonresponders with Open-Angle Glaucoma in the Japanese Population", Japanese Journal of Ophthalmology, vol. 50, No. 2, 2006, pp. 153-157.

Kalouche, et al., "Activation of Prostaglandin FP and EP2 Receptors Differently Modulates Myofibroblast Transition in a Model of Adult Primary Human Trabecular Meshwork Cells", Investigative Ophthalmology & Visual Science, vol. 57, No. 4, 2016, pp. 1816-1825.

Kim, et al., "Biocompatibility and Pharmacokinetic Analysis of an Intracameral Polycaprolactone Drug Delivery Implant for Glaucoma", Investigative Ophthalmology & Visual Science, vol. 57, No. 10, 2016, pp. 4341-4346.

Kocluk, et al., "Efficacy of Monotherapy with Either Bimatoprost or Travoprost in Patients with Primary Open-Angle Glaucoma Resistant to Latanoprost Therapy", Turkish Journal of Ophthalmology, vol. 41, No. 5, pp. 295-298, with partial English translation.

Lu, et al., "A Phase 3 Trial Comparing Omidenepag Isopropyl 0.002% with Latanoprost 0.005% in Primary Open-Angle Glaucoma and Ocular Hypertension: The Ayame Study", Investigative Ophthalmology & Visual Science, vol. 59, Jul. 2018, p. 1235. (2 pages).

(Continued)

*Primary Examiner* — Niloofar Rahmani
(74) *Attorney, Agent, or Firm* — BUCHANAN INGERSOLL & ROONEY PC

(57) ABSTRACT

The present invention aims to find a pharmaceutical preparation which treats or prevents glaucoma or ocular hypertension and is effective for patients with inadequate efficacies of glaucoma or ocular hypertension therapeutic agents. It has been found that omidenepag, an ester thereof, or a salt thereof has an excellent intraocular pressure lowering efficacy on patients with inadequate efficacies of other glaucoma or ocular hypertension therapeutic agents. Therefore, the omidenepag, the ester thereof, or the salt thereof of the present invention is useful as a pharmaceutical preparation which can treat or prevent glaucoma or ocular hypertension even in patients with inadequate efficacies of other glaucoma or ocular hypertension therapeutic agents.

10 Claims, 1 Drawing Sheet

(56) References Cited

OTHER PUBLICATIONS

Odani, Noriko, "Development of Intraocular Pressure Lowering Drugs of a New Action Mechanism-Selective EP2 Receptor Agonists, Omidenepag Isopropyl Ophthalmic Solution", Programs and lecture abstracts of the 37th Annual Scientific Meeting of the Japanese Society for Ocular Pharmacology, Sep. 2017, with an English translation. (6 pages).
International Search Report (PCT/ISA/210) mailed on Mar. 12, 2019, by the Japan Patent Office as the International Searching Authority for International Application No. PCT/JP2018/048228. (5 pages).
Written Opinion (PCT/ISA/237) mailed on Mar. 12, 2019, by the Japan Patent Office as the International Searching Authority for International Application No. PCT/JP2018/048228. (12 pages).
Ropo, et al., "IOP Lowering Effect of Omidenepag Isopropyl in Latanoprost Non-/Low-Responder Subjects with Primary Open-Angle Glaucoma or Ocular Hypertension: The Fuji Study", Investigative Ophthalmology & Visual Science, vol. 59, No. 9, Jul. 2018. (4 pages).
Schmier, et al., "Adjunctive Therapy Patterns in Glaucoma Patients using Prostaglandin Analogs", Clinical Ophthalmology, vol. 8, 2014, pp. 1097-1104.
Taniguchi, et al., "Omidenepag isopropyl, a Selective EP2 Agonist, Shows Additive Intraocular Pressure (IOP)-Lowering Effects when used Concomitantly with Existing Anti-Glaucoma Drugs in Animal Models", Investigative Ophthalmology & Visual Science, vol. 58, No. 8, Jun. 2017, p. 2105. (2 pages).
Williams, Robert D., "Efficacy of Bimatoprost in Glaucoma and Ocular Hypertension Unresponsive to Latanoprost", Advances in Therapy, vol. 19, No. 6, 2002, pp. 275-281.

\* cited by examiner

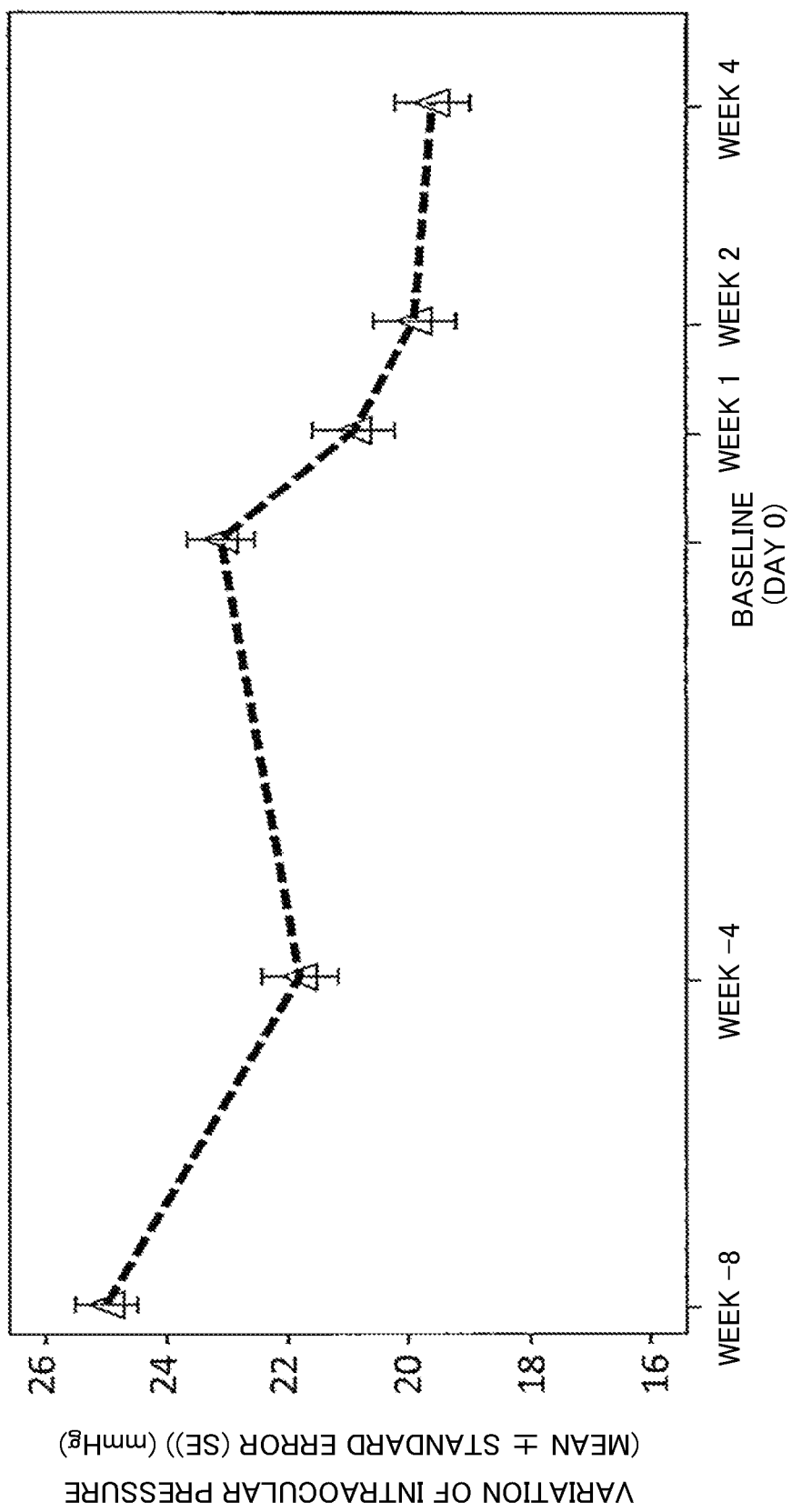

PHARMACEUTICAL PREPARATION CONTAINING PYRIDYL AMINOACETIC ACID COMPOUND

CROSS REFERENCE OF RELATED APPLICATIONS

This application is a continuation of U.S. patent application Ser. No. 16/957,749, filed on Jun. 25, 2020, entitled "PHARMACEUTICAL PREPARATION CONTAINING PYRIDYL AMINOACETIC ACID COMPOUND," which in turn is a national stage application of PCT/JP2018/048228, filed on Dec. 27, 2018, which claims priority to U.S. Provisional Application No. 62/611,017, filed Dec. 28, 2017. The entire content of each of the prior applications is hereby incorporated by reference.

TECHNICAL FIELD

The present invention relates to a pharmaceutical preparation which treats or prevents glaucoma or ocular hypertension, containing omidenepag, an ester thereof, or a salt thereof as an active ingredient, in which the pharmaceutical preparation is administered to a patient with inadequate efficacies of other glaucoma or ocular hypertension therapeutic agents.

BACKGROUND ART

Glaucoma is an intractable ophthalmic disease in which intraocular pressure increases due to various pathological reasons to impair internal tissues of the eyeball (such as the retina and the optic nerve), possibly leading to blindness. As a method of treating glaucoma, intraocular pressure lowering therapy is general, and typical examples thereof include drug therapy, laser therapy, and surgery therapy.

Drugs used in drug therapy include sympathomimetics (non-selective stimulants such as dipivefrine, and $\alpha_2$-receptor agonists such as brimonidine), sympatholytics ($\beta$-receptor blockers such as timolol, befunolol, carteolol, nipradilol, betaxolol, levobunolol, and metipranolol, and al-receptor blockers such as bunazosin hydrochloride), parasympathomimetics (such as pilocarpine), carbonic anhydrase inhibitors (such as acetazolamide), prostaglandins (such as isopropyl unoprostone, latanoprost, travoprost, and bimatoprost), Rho kinase inhibitors (ripasudil), and the like.

Among these drugs, latanoprost-containing eye drops have been widely used in various countries in the world since their international birth in 1996 due to their strong intraocular pressure lowering efficacy and good tolerability. However, it is known that there are a certain number of patients with an inadequate effect by latanoprost.

Meanwhile, omidenepag is a compound described as one of an enormous number of pyridyl aminoacetic acid compounds in Patent Literature 1 and Patent Literature 2. It is stated that these pyridyl aminoacetic acid compounds have an EP2 agonistic activity (Patent Literature 2), and thus are expected to have an intraocular pressure lowering efficacy and can be a therapeutic agent for glaucoma (Patent Literature 1).

Moreover, Patent Literatures 3 and 4 state that the intraocular pressure lowering efficacy is enhanced by combining omidenepag with another glaucoma therapeutic agent such as timolol, Patent Literature 5 states that omidenepag at a specific content exhibits a particularly excellent intraocular pressure lowering efficacy, and Patent Literature 6 states that omidenepag is useful as a therapeutic agent for diseases accompanied by highly elevated intraocular pressure.

In addition, Patent Literatures 7 to 9 describe specific preparations containing omidenepag as an active ingredient.

Note that the entire contents of Patent Literatures 1 to 9 and the other literatures described in the present specification are incorporated as the disclosure of the present specification.

However, none of the literatures describes what efficacy omidenepag, an ester thereof, or a salt thereof has on patients with inadequate efficacies of other glaucoma or ocular hypertension therapeutic agents, and there are no other literatures or research reports on such efficacies.

CITATION LIST

Patent Literatures

Patent Literature 1: Unites States Patent Application Publication No. 2012/0190852
Patent Literature 2: Unites States Patent Application Publication No. 2011/0054172
Patent Literature 3: Unites States Patent Application Publication No. 2014/0018396
Patent Literature 4: Unites States Patent Application Publication No. 2014/0018350
Patent Literature 5: Unites States Patent Application Publication No. 2015/0196541
Patent Literature 6: International Publication No. WO2017/006985
Patent Literature 7: Unites States Patent Application Publication No. 2016/0317512
Patent Literature 8: Unites States Patent Application Publication No. 2016/0317664
Patent Literature 9: International Publication No. WO2017/002941

SUMMARY OF INVENTION

It is a very interesting task to find a pharmaceutical preparation which treats or prevents glaucoma or ocular hypertension and is effective for patients with inadequate efficacies of glaucoma or ocular hypertension therapeutic agents.

Means for Solution of the Problems

In view of the above, the present inventors have made earnest studies and have found as a result that omidenepag, an ester thereof, or a salt thereof has an excellent intraocular pressure lowering efficacy on patients with inadequate efficacies of other glaucoma or ocular hypertension therapeutic agents. Thus, the present invention has been completed. Specifically, the present invention provides the following.

[1]

A pharmaceutical preparation which treats or prevents glaucoma or ocular hypertension, comprising: omidenepag, an ester thereof, or a salt thereof as an active ingredient, wherein the pharmaceutical preparation is administered to a patient with inadequate efficacies of other glaucoma or ocular hypertension therapeutic agents.

[2]

The pharmaceutical preparation according to [1] described above, wherein the treatment or prevention of glaucoma or ocular hypertension includes treating or preventing glaucoma or ocular hypertension with the other glaucoma or ocular hypertension therapeutic agents and then further treating or preventing glaucoma or ocular hypertension by lowering intraocular pressure with the active ingredient.

[3]

The pharmaceutical preparation according to [1] or [2] described above, wherein an active ingredient of the other glaucoma or ocular hypertension therapeutic agents is a prostaglandin $F_{2\alpha}$ derivative.

[4]

The pharmaceutical preparation according to any one of [1] to [3] described above, wherein an active ingredient of the other glaucoma or ocular hypertension therapeutic agents is latanoprost.

[5]

The pharmaceutical preparation according to any one of [1] to [4] described above, wherein a content of the omidenepag, the ester thereof, or the salt thereof is 0.001 to 0.003% (w/v).

[6]

The pharmaceutical preparation according to any one of [1] to [5] described above, wherein a content of the omidenepag, the ester thereof, or the salt thereof is 0.002% (w/v).

[7]

The pharmaceutical preparation according to any one of [1] to [6] described above, wherein the omidenepag, the ester thereof, or the salt thereof is omidenepag isopropyl.

[8]

The pharmaceutical preparation according to any one of [1] to [7] described above, which is an eye drop.

[9]

A pharmaceutical preparation which treats or prevents glaucoma or ocular hypertension, comprising: omidenepag, an ester thereof, or a salt thereof as an active ingredient, wherein the glaucoma is glaucoma resistant to treatment of glaucoma with other active ingredients other than the omidenepag, the ester thereof, or the salt thereof, and the ocular hypertension is ocular hypertension resistant to treatment of ocular hypertension with the other active ingredients.

[10]

A method of treating or preventing glaucoma or ocular hypertension, comprising: administering to a patient a pharmaceutical preparation containing omidenepag, an ester thereof, or a salt thereof as an active ingredient, wherein the patient is a patient with inadequate efficacies of other glaucoma or ocular hypertension therapeutic agents.

[11]

The method according to described above, wherein the treatment or prevention of glaucoma or ocular hypertension includes treating or preventing glaucoma or ocular hypertension with the other glaucoma or ocular hypertension therapeutic agents and then further treating or preventing glaucoma or ocular hypertension by lowering intraocular pressure with the active ingredient.

[12]

The method according to or described above, wherein an active ingredient of the other glaucoma or ocular hypertension therapeutic agents is a prostaglandin $F_{2\alpha}$ derivative.

[13]

The method according to any one of to described above, wherein an active ingredient of the other glaucoma or ocular hypertension therapeutic agents is latanoprost.

[14]

The method according to any one of to described above, wherein a content of the omidenepag, the ester thereof, or the salt thereof in the pharmaceutical preparation is 0.001 to 0.003% (w/v).

[15]

The method according to any one of to described above, wherein a content of the omidenepag, the ester thereof, or the salt thereof in the pharmaceutical preparation is 0.002% (w/v).

[16]

The method according to any one of to described above, wherein the omidenepag, the ester thereof, or the salt thereof is omidenepag isopropyl.

[17]

The method according to any one of to described above, wherein the administration is ophthalmic administration.

[18]

A method of treating or preventing glaucoma or ocular hypertension, comprising: administering to a patient a pharmaceutical preparation containing omidenepag, an ester thereof, or a salt thereof as an active ingredient, wherein the glaucoma is glaucoma resistant to treatment of glaucoma with other active ingredients other than the omidenepag, the ester thereof, or the salt thereof, and the ocular hypertension is ocular hypertension resistant to treatment of ocular hypertension with the other active ingredients.

[19]

A method of treating or preventing glaucoma or ocular hypertension including administering to a patient a pharmaceutical preparation containing omidenepag, an ester thereof, or a salt thereof as an active ingredient, the method comprising the following steps:

(1) a first treatment step of administering to a patient a other glaucoma or ocular hypertension therapeutic agent other than omidenepag, an ester thereof, or a salt thereof:

(2) a step of judging whether the first treatment step is inadequate in treatment or inadequate in preventive effect; and (3) a second treatment step of further administering to a patient a pharmaceutical preparation containing omidenepag, an ester thereof, or a salt thereof as an active ingredient when the first treatment step is inadequate in treatment or inadequate in preventive effect.

[20]

Use of the pharmaceutical preparation according to any one of [1] to [9] described above in the manufacture of a medicament which treats or prevents glaucoma or ocular hypertension.

Note that two or more of the above configurations [1] to [20] can be optionally selected and combined.

As explained in detail in the examples to be described later, it has been found that omidenepag, an ester thereof, or a salt thereof has an excellent intraocular pressure lowering efficacy on patients with inadequate efficacies of other glaucoma or ocular hypertension therapeutic agents. Therefore, the omidenepag, the ester thereof, or the salt thereof is useful as a pharmaceutical preparation which treats or prevents glaucoma or ocular hypertension even in patients with inadequate efficacies of other glaucoma or ocular hypertension therapeutic agents.

BRIEF DESCRIPTION OF DRAWINGS

FIG. 1 is a graph illustrating a change over time in the variation of intraocular pressure in a clinical test.

DESCRIPTION OF EMBODIMENTS

Hereinafter, embodiments of the present invention is described in detail.

[Pharmaceutical Preparation]

Omidenepag contained in the pharmaceutical preparation of the present invention is a compound represented by the following formula (1) (CAS registration number; 1187451-41-7):

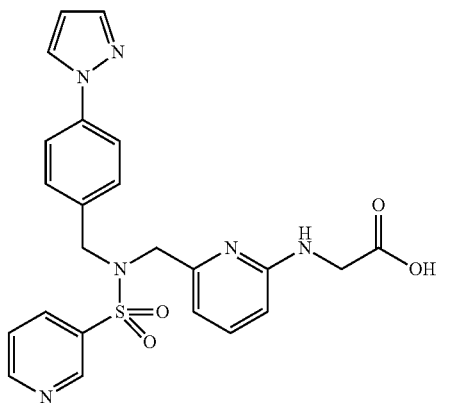

(1)

and is also referred to as (6-{[4-(pyrazol-1-yl)benzyl](pyridin-3-ylsulfonyl)aminomethyl}pyridin-2-ylamino)acetic acid.

The ester of omidenepag contained in the pharmaceutical preparation of the present invention is preferably an ester formed by dehydration condensation of a carboxyl group of omidenepag with a monohydric alcohol having 1 to 6 carbon atoms, and suitably an ester formed by dehydration condensation of a carboxyl group of omidenepag with a monohydric alcohol more preferably having 2 to 5 carbon atoms and further preferably having 3 or 4 carbon atoms. Specific esters include methyl esters, ethyl esters, n-propyl esters, isopropyl esters, n-butyl esters, isobutyl esters, sec-butyl esters, tert-butyl esters, n-pentyl esters, and n-hexyl esters, more preferably ethyl esters, n-propyl esters, isopropyl esters, and more preferably isopropyl esters. A specific isopropyl ester of omidenepag is a compound represented by the following formula (2) (CAS registration number; 1187451-19-9):

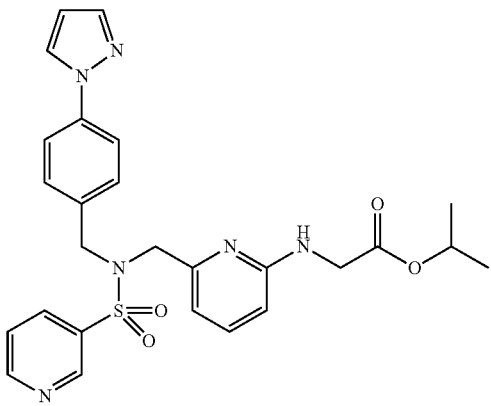

(2)

and is also referred to as omidenepag isopropyl or isopropyl (6-{[4-(pyrazol-1-yl)benzyl](pyridin-3-ylsulfonyl)aminomethyl}pyridin-2-ylamino)acetate.

The salt of omidenepag or ester salt of omidenepag contained in the pharmaceutical preparation of the present invention is not particularly limited as long as it is a pharmacologically acceptable salt. Specific examples include inorganic acid salts such as hydrochlorides, hydrobromides, hydroiodides, nitrates, sulfates, and phosphates: organic acid salts such as acetates, trifluoroacetates, benzoates, oxalates, malonates, succinates, maleates, fumarates, tartrates, citrates, methanesulfonates, ethanesulfonates, trifluoromethane sulfonates, benzene sulfonates, p-toluene sulfonates, glutamates, and aspartates; metal salts such as sodium salts, potassium salts, calcium salts, and magnesium salts; inorganic salts such as ammonium salts; and organic amine salts such as triethylamine salts or guanidine salts, and preferably include hydrochlorides and trifluoroacetates.

The omidenepag, the ester thereof, or the salt thereof contained in the pharmaceutical preparation of the present invention can be produced according to e.g. a normal method in the technical field and the methods described in Unites States Patent Application Publication No. 2012/0190852 (Patent Literature 1) and Unites States Patent Application Publication No. 2011/0054172 (Patent Literature 2). In the production methods, the scope of the content of omidenepag, an ester thereof, or a salt thereof contained in the pharmaceutical preparation of the present invention, the type and amount of the additive, the route of administration, and the like can employ the modes as described in the above literatures. Note that the term "omidenepag, an ester thereof, or a salt thereof" used in the present application is meant to include (1) omidenepag, (2) an ester of omidenepag, (3) a salt of omidenepag, and (4) an ester salt of omidenepag.

The content of omidenepag, an ester thereof, or a salt thereof contained in the pharmaceutical preparation of the present invention is not particularly limited and depends on the route of administration, and the lower limit thereof is, for example, 0.000001% (w/v), preferably 0.00001% (w/v), more preferably 0.00003% (w/v), 0.0001% (w/v), 0.001 (w/v), 0.01% (w/v), 0.1% (w/v), or 1% (w/v). The upper limit of the above content may be, for example, 30% (w/v), 25% (w/v), 20% (w/v), 15% (w/v), or 12% (w/v), or 0.03% (w/v), 0.01% (w/v), 0.005% (w/v), 0.003% (w/v), or 0.0027% (w/v). More specifically, the above content may be a range formed by combining any of the above lower limits and upper limits, and is, for example, 0.000001 to 30% (w/v), preferably 0.00001 to 25% (w/v), more preferably 0.00003 to 20% (w/v), further preferably 0.0001 to 15% (w/v), particularly preferably 0.0013 to 12% (w/v), and especially preferably 0.0015 to 10% (w/v). Here, "% (w/v)" means the mass (g) of an active ingredient (omidenepag, an ester thereof, or a salt thereof) or an additive (such as a surfactant) contained in 100 mL of the pharmaceutical preparation. For example, omidenepag at 0.01% (w/v) means that the content of omidenepag contained in 100 mL of the pharmaceutical preparation is 0.01 g.

When the pharmaceutical preparation of the present invention is an eye drop, the lower limit of the content of omidenepag, an ester thereof, or a salt thereof contained in the pharmaceutical preparation of the present invention is preferably 0.0003% (w/v), more preferably 0.001% (w/v), further preferably 0.0013% (w/v), and particularly preferably 0.0015% (w/v). In addition, the upper limit of the above content is preferably 0.03% (w/v), more preferably 0.01% (w/v), further preferably 0.005% (w/v), particularly preferably 0.003% (w/v), and especially preferably 0.0027% (w/v). More specifically, the above content may be a range formed by combining any of the above lower limits and upper limits, and is preferably 0.0003 to 0.03% (w/v), more preferably 0.001 to 0.01% (w/v), further preferably 0.001 to 0.005% (w/v), particularly preferably 0.001 to 0.003% (w/v), especially preferably 0.0013 to 0.003% (w/v), and highly especially preferably 0.0015 to 0.0027% (w/v). In further detail, preferable are 0.0010% (w/v), 0.0011% (w/v), 0.0012% (w/v), 0.0013% (w/v), 0.0014% (w/v), 0.0015% (w/v), 0.0016% (w/v), 0.0017% (w/v), 0.0018% (w/v), 0.0019% (w/v), 0.0020% (w/v), 0.0021% (w/v), 0.0022% (w/v), 0.0023% (w/v), 0.0024% (w/v), 0.0025% (w/v), 0.0026% (w/v), 0.0027% (w/v), 0.0028% (w/v), 0.0029% (w/v), 0.0030% (w/v), 0.005% (w/v), 0.01% (w/v), 0.03% (w/v), and a range including the above quantities as the upper limit or the lower limit, and 0.002% (w/v) is most preferable. Note that the above content is a preferable example for an eye drop, but is not limited to an eye drop.

When the pharmaceutical preparation of the present invention is an ophthalmic injection, the lower limit of the content of omidenepag, an ester thereof, or a salt thereof contained in the pharmaceutical preparation of the present invention is preferably 0.000001% (w/v), more preferably 0.000003 (w/v), further preferably 0.000005% (w/v), particularly preferably 0.00001% (w/v), and especially preferably 0.00003% (w/v). In addition, the upper limit of the above content is preferably 30% (w/v), more preferably 10% (w/v), further preferably 1% (w/v), particularly preferably 0.1% (w/v), and especially preferably 0.01% (w/v). More specifically, the above content may be a range formed by combining any of the above lower limits and upper limits, and is preferably 0.000001 to 30% (w/v), more preferably 0.000003 to 10% (w/v), further preferably 0.000005 to 1% (w/v), particularly preferably 0.00001 to 0.1% (w/v), and especially preferably 0.00003 to 0.01% (w/v). Note that the above content is a preferable example for an ophthalmic injection, but is not limited to an ophthalmic injection.

Note that, the case where the pharmaceutical preparation of the present invention contains a salt of omidenepag or an ester thereof, it means that the content of omidenepag or an ester thereof falls within the above range when the salt is released.

[Additive]

An additive can be used in the pharmaceutical preparation of the present invention as necessary. As an additive, for example, it is possible to add surfactants, buffer agents, tonicity adjusting agents, stabilizers, preservatives, antioxidants, thickeners, bases, pH adjusters, and the like.

The pharmaceutical preparation of the present invention can be appropriately blended with a surfactant that can be used as a pharmaceutical additive.

Examples of the surfactant include polyoxyethylene castor oils, polyoxyethylene hydrogenated castor oils, polyoxyethylene sorbitan fatty acid esters, vitamin E TPGS, polyoxyethylene fatty acid esters, polyoxyethylene polyoxypropylene glycol, sucrose fatty acid esters, and the like.

More specifically, as the polyoxyethylene castor oils, it is possible to use various polyoxyethylene castor oils having different degrees of polymerization of ethylene oxide, and the degree of polymerization of ethylene oxide is preferably 5 to 100, more preferably 20 to 50, particularly preferably 30 to 40, and most preferably 35. Specific examples of the polyoxyethylene castor oils include polyoxyl 5 castor oil, polyoxyl 9 castor oil, polyoxyl 15 castor oil, polyoxyl 35 castor oil, polyoxyl 40 castor oil, and the like, and polyoxyl 35 castor oil is most preferable.

As the polyoxyethylene hydrogenated castor oils, it is possible to use various polyoxyethylene hydrogenated castor oils having different degrees of polymerization of ethylene oxide, and the degree of polymerization of ethylene oxide is preferably 10 to 100, more preferably 20 to 80, particularly preferably 40 to 70, and most preferably 60. Specific examples of the polyoxyethylene hydrogenated castor oil include polyoxyethylene hydrogenated castor oil 10, polyoxyethylene hydrogenated castor oil 40, polyoxyethylene hydrogenated castor oil 50, polyoxyethylene hydrogenated castor oil 60, and polyoxyethylene hydrogenated castor oil 60 is most preferable.

The polyoxyethylene sorbitan fatty acid esters include Polysorbate 80, Polysorbate 60, Polysorbate 40, polyoxyethylene sorbitan monolaurate, polyoxyethylene sorbitan trioleate, Polysorbate 65, and the like, and Polysorbate 80 is most preferable.

Vitamin E TPGS is also referred to as tocopherol polyethylene glycol 1000 succinate.

The polyoxyethylene fatty acid esters include polyoxyl 40 stearate and the like.

The polyoxyethylene polyoxypropylene glycol includes polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and the like.

The sucrose fatty acid esters include sucrose stearate ester.

When the pharmaceutical preparation of the present invention is blended with a surfactant, the content thereof can be appropriately adjusted depending on the type and the like of the surfactant. Specifically, the lower limit is preferably 0.001% (w/v), more preferably 0.01% (w/v), further preferably 0.1% (w/v), particularly preferably 0.5% (w/v), and most preferably 0.8% (w/v). The upper limit is preferably 10% (w/v), more preferably 5% (w/v), further preferably 4% (w/v), particularly preferably 3% (w/v), and most preferably 2% (w/v). More specifically, the content may be a range formed by combining any of the above lower limits and upper limits, and is preferably 0.001 to 10% (w/v), more preferably 0.01 to 5% (w/v), further preferably 0.03 to 4% (w/v), particularly preferably 0.05 to 3% (w/v), and most preferably 0.1 to 2% (w/v).

The pharmaceutical preparation of the present invention can be appropriately blended with a buffer agent that can be used as a pharmaceutical additive.

Examples of the buffer agent include phosphoric acid or a salt thereof, boric acid or a salt thereof, citric acid or a salt thereof, acetic acid or a salt thereof, carbonic acid or a salt thereof, tartaric acid or a salt thereof, ε-aminocaproic acid, trometamol, and the like. More specifically, phosphates include sodium phosphate, sodium dihydrogen phosphate, disodium hydrogen phosphate, potassium phosphate, potassium dihydrogen phosphate, dipotassium hydrogen phosphate, and the like, borates include borax, sodium borate, and potassium borate, citric acid or a salt thereof includes citric acid monohydrate, sodium citrate, disodium citrate, trisodium citrate, and the like, acetates include sodium acetate, potassium acetate, and the like, carbonates include sodium carbonate, sodium bicarbonate, and the like, and tartrates include sodium tartrate, potassium tartrate, and the like. Among these, boric acid or a salt thereof, or citric acid or a salt thereof is preferable.

When the pharmaceutical preparation of the present invention is blended with a buffer agent, the content thereof can be appropriately adjusted depending on the type and the like of buffering agent, and is preferably 0.001 to 10% (w/v), more preferably 0.01 to 5% (w/v), further preferably 0.05 to 3% (w/v), and most preferably 0.1 to 2% (w/v).

The pharmaceutical preparation of the present invention can be appropriately blended with a tonicity adjusting agent that can be used as a pharmaceutical additive.

Examples of the tonicity adjusting agent include ionic tonicity adjusting agents and nonionic tonicity adjusting agents.

The ionic tonicity adjusting agents include sodium chloride, potassium chloride, calcium chloride, magnesium chloride, and the like, and the nonionic tonicity adjusting agents include glycerin, propylene glycol, sorbitol, mannitol, and the like. When the pharmaceutical preparation of the present invention is blended with a tonicity adjusting agent, the content thereof can be appropriately adjusted depending on the type and the like of the tonicity adjusting agent, and is preferably 0.01 to 10% (w/v), more preferably 0.02 to 7% (w/v), further preferably 0.1 to 5% (w/v), particularly preferably 0.5 to 4% (w/v), and most preferably 0.8 to 3% (w/v).

The pharmaceutical preparation of the present invention can be appropriately blended with a stabilizer that can be used as a pharmaceutical additive.

Examples of the stabilizer include edetic acid, monosodium edetate, disodium edetate, tetrasodium edetate, sodium citrate, and the like, and disodium edetate is particularly preferable. Edetate sodium may be a hydrate. When the pharmaceutical preparation of the present invention is blended with a stabilizer, the content thereof can be appropriately adjusted depending on the type and the like of the stabilizer, preferably 0.001 to 1% (w/v), more preferably 0.005 to 0.5% (w/v), and most preferably 0.01 to 0.1% (w/v).

The pharmaceutical preparation of the present invention can be appropriately blended with a preservative that can be used as a pharmaceutical additive.

Examples of the preservative include benzalkonium chloride, benzalkonium bromide, benzethonium chloride, sorbic acid, potassium sorbate, methyl paraoxy benzoate, propyl paraoxybenzoate, chlorobutanol, and the like. When the pharmaceutical preparation of the present invention is blended with a preservative, the content thereof can be appropriately adjusted depending on the type and the like of the preservative, and is preferably 0.0001 to 1% (w/v), more preferably 0.0005 to 0.1% (w/v), further preferably 0.001 to 0.05% (w/v), and most preferably 0.005 to 0.010% (w/v). Moreover, the case where a preservative is not contained is also preferable.

The pharmaceutical preparation of the present invention can be appropriately blended with an antioxidant that can be used as a pharmaceutical additive.

Examples of the antioxidant include ascorbic acid, tocophenol, dibutylhydroxytoluene, butylhydroxyanisole, sodium erythorbate, propyl gallate, sodium sulfite, and the like. When the pharmaceutical preparation of the present invention is blended with an antioxidant, the content thereof can be appropriately adjusted depending on the type and the like of the antioxidant, and is preferably 0.0001 to 1% (w/v), more preferably 0.0005 to 0.1% (w/v), and most preferably 0.001 to 0.05% (w/v).

The pharmaceutical preparation of the present invention can be appropriately blended with a thickener that can be used as a pharmaceutical additive.

Examples of the thickener include methyl cellulose, ethyl cellulose, hydroxymethyl cellulose, hydroxyethyl cellulose, hydroxypropyl cellulose, hydroxyethyl methyl cellulose, hydroxypropyl methyl cellulose, carboxymethyl cellulose, sodium carboxymethyl cellulose, hydroxypropyl methylcellulose acetate succinate, hydroxypropyl methylcellulose phthalate, carboxymethylethylcellulose, cellulose acetate phthalate, polyvinyl pyrrolidone, polyvinyl alcohol, carboxyvinyl polymer, polyethylene glycol, and the like.

When the pharmaceutical preparation of the present invention is blended with a thickener, the content thereof can be appropriately adjusted depending on the type and the like of the thickener, and is preferably 0.001 to 5% (w/v), more preferably 0.01 to 1% (w/v), and most preferably 0.1 to 0.5% (w/v).

The pharmaceutical preparation of the present invention can be appropriately blended with a base that can be used as a pharmaceutical additive.

Examples of the base include water, physiological saline, dimethyl sulfoxide, polyethylene glycols such as PEG 400, tributyl citrate, acetyltributyl citrate, benzyl benzoate, white petrolatum, liquid paraffin, and the like, and water, physiological saline, dimethyl sulfoxide, and PEG 400 are preferable.

The pH of the pharmaceutical preparation of the present invention is preferably 4.0 to 8.0, more preferably 4.5 to 7.5, particularly preferably 5.0 to 7.0, and most preferably 5.5 to 6.1. In addition, the pH may be 6.0 to 8.0. The pharmaceutical preparation of the present invention may be added with a PH adjuster for adjusting the pH, such as hydrochloric acid, phosphoric acid, citric acid, acetic acid, sodium hydroxide, and potassium hydroxide.

[Usage]

The pharmaceutical preparation of the present invention exhibits an excellent intraocular pressure lowering efficacy even on patients with inadequate efficacies of other glaucoma or ocular hypertension therapeutic agents, and thus is useful as a glaucoma treatment or prevention agent and/or an ocular hypertension treatment or prevention agent and/or an intraocular pressure lowering agent. The glaucoma in the present invention includes primary open angle glaucoma, secondary open angle glaucoma, normal tension glaucoma, hypersecretion glaucoma, primary angle closure glaucoma, secondary angle closure glaucoma, plateau iris glaucoma, mixed glaucoma, developmental glaucoma, steroid glaucoma, exfoliation glaucoma, amyloid glaucoma, neovascular glaucoma, malignant glaucoma, capsular glaucoma of the lens, plateau iris syndrome, and the like, and preferably primary open angle glaucoma, normal tension glaucoma, and primary angle closure glaucoma. In particular, the pharmaceutical preparation of the present invention is effective for primary open angle glaucoma.

Preferably, the pharmaceutical preparation of the present invention is administered to patients with inadequate efficacies of other glaucoma or ocular hypertension therapeutic agents. The other glaucoma or ocular hypertension therapeutic agents refer to any glaucoma or ocular hypertension therapeutic agent containing an active ingredient other than omidenepag, an ester thereof, or a salt thereof (other active ingredient), and specific examples of the active ingredient other than omidenepag, an ester thereof, or a salt thereof include non-selective sympathomimetics, $\alpha_2$-receptor agonists, $\alpha_1$-receptor blockers, $\beta$-receptor blockers, parasympathomimetics, carbonic anhydrase inhibitors, prostaglandins, and Rho kinase inhibitors. Specific examples of the non-selective sympathomimetics include dipivefrine, specific examples of the $\alpha_2$-receptor agonists include brimonidine and apraclonidine, specific examples of the $\alpha_1$-receptor blockers include bunazosin, specific examples of the $\beta$-receptor blockers include timolol, befunolol, carteolol, nipradilol, betaxolol, levobunolol, and metipranolol, specific examples of the parasympathomimetics include pilocarpine, specific examples of the carbonic anhydrase inhibitors include dorzolamide, brinzolamide, and acetazolamide, specific examples of the prostaglandins include latanoprost, isopropyl unoprostone, bimatoprost, and travoprost, and specific examples of Rho kinase inhibitors include fasudil. Among these, prostaglandins are preferable, prostaglandin $F_{2\alpha}$ derivatives are more preferable, latanoprost is further preferable, latanoprost ophthalmic solution is particularly preferable, and 0.005% latanoprost ophthalmic solution is most preferable.

The patients with inadequate efficacies of other glaucoma or ocular hypertension therapeutic agents are patients who cannot benefit from sufficient efficacies by treatment with other glaucoma or ocular hypertension therapeutic agents. Specifically, the patients are preferably such that, when subjected to treatment with other glaucoma or ocular hypertension therapeutic agents, the rate of decrease between pre-treatment intraocular pressure and post-treatment intraocular pressure (rate of decrease in intraocular pressure: [pre-treatment intraocular pressure (mmHg)-post-treatment intraocular pressure (mmHg)]/[pre-treatment intraocular pressure (mmHg)]×100) is 18% or less, preferably 17% or less, more preferably 16% or less, further preferably 15% or less, even more preferably 14% or less, especially preferably 13% or less, particularly preferably 12% or less, and most preferably 10% or less. In addition, the patients are also preferably such that, when subjected to treatment with other glaucoma or ocular hypertension therapeutic agents, the width of decrease between pre-treatment intraocular pressure and post-treatment intraocular pressure (=variation of intraocular pressure: [pre-treatment intraocular pressure (mmHg)-post-treatment intraocular pressure (mmHg)]) is 4.5 mmHg or less, preferably 4.2 mmHg or less, more preferably 4 mmHg or less, further preferably 3.7 mmHg or less, even more preferably 3.5 mmHg or less, especially preferably 3.2 mmHg or less, particularly preferably 3 mmHg or less, and most preferably 2.5 mmHg or less. This treatment with other glaucoma or ocular hypertension therapeutic agents is usually carried out by ophthalmic administration of one to three drops at a time and one to three times a day for a period of one week or more, preferably two weeks or more, more preferably four weeks or more, further preferably two months or more, particularly preferably six months or more, and most preferably one year or more. In addition, the patients with inadequate efficacies of other glaucoma or ocular hypertension therapeutic agents include patients who cannot be treated or cannot use other glaucoma or ocular hypertension therapeutic agents due to side effects and the like. Note that the patients targeted by the pharmaceutical preparation of the present invention are mammals including domestic animals such as cows and pigs, rabbits, monkeys, dogs, cats, and humans, and preferably humans.

On the other hand, the pharmaceutical preparation of the present invention makes it possible to further lower the intraocular pressure of a patient under treatment with other glaucoma or ocular hypertension therapeutic agents even in the case of a rate of decrease in intraocular pressure and a variation of intraocular pressure to such a degree that the efficacies are considered inadequate as described above. The rate of decrease between pre-treatment intraocular pressure and post-treatment intraocular pressure (rate of decrease in intraocular pressure) attributed to the pharmaceutical preparation of the present invention is suitably at least 5%, for example 6% or more, preferably 7% or more, more preferably 8% or more, further preferably 9% or more, even more preferably 10% or more, especially preferably 11% or more, particularly preferably 12% or more, and most preferably 13% or more. The upper limit value of the rate of decrease in intraocular pressure attributed to the pharmaceutical preparation of the present invention can be, for example, 40% or less, preferably 35% or less, more preferably 30% or less, further preferably 28% or less, even more preferably 26% or less, especially preferably 24% or less, particularly preferably 22% or less, and most preferably 20% or less. It is possible to appropriately select a range formed by appropriately combining any of the above lower limit values and upper limit values. A preferable rate of decrease in intraocular pressure attributed to the pharmaceutical preparation of the present invention is, for example, 5 to 40%, preferably 7 to 35%, and more preferably 9 to 30%.

In addition, by virtue of the pharmaceutical preparation of the present invention, the width of decrease between pre-treatment intraocular pressure and post-treatment intraocular pressure (variation of intraocular pressure) attributed to the pharmaceutical preparation of the present invention is suitably at least 1.0 mmHg or more, preferably 1.2 mmHg or more, more preferably 1.4 mmHg or more, further preferably 1.6 mmHg or more, even more preferably 1.8 mmHg or more, especially preferably 2.0 mmHg or more, particularly preferably 2.5 mmHg or more, and most preferably 2.9 mmHg or more. The upper limit value of the variation of intraocular pressure attributed to the pharmaceutical preparation of the present invention can be, for example, 10.0 mmHg or less, preferably 8.0 mmHg or less, more preferably 6.0 mmHg or less, further preferably 5.5 mmHg or less, even more preferably 5.0 mmHg or less, especially preferably 4.5 mmHg or less, particularly preferably 4.0 mmHg or less, and most preferably 3.2 mmHg or less. It is possible to appropriately select a range formed by appropriately combining any of the above lower limit values and upper limit values. A preferable variation of intraocular pressure attributed to the pharmaceutical preparation of the present invention is, for example, 1.0 to 10.0 mmHg, preferably 1.4 to 8.0 mmHg, and more preferably 1.8 to 6.0 mmHg.

Note that the "rate of decrease between pre-treatment intraocular pressure and post-treatment intraocular pressure (rate of decrease in intraocular pressure) attributed to the pharmaceutical preparation of the present invention" and the "width of decrease (variation of intraocular pressure)" defined here mean the rate of decrease and width of decrease in intraocular pressure in the second treatment step as indicated in (3) of [Administration Method] to be described later, but do not include the rate of decrease in intraocular pressure and variation of intraocular pressure due to the treatment with other glaucoma or ocular hypertension therapeutic agents as in the first treatment step indicated in (1) of [Administration Method]. Therefore, the pharmaceutical preparation of the present invention containing omidenepag or the like as an active ingredient can lower intraocular pressure in addition to the therapeutic efficacies of the other glaucoma or ocular hypertension therapeutic agents containing latanoprost and the like as active ingredients.

In order to more strongly lower intraocular pressure, the pharmaceutical preparation of the present invention may be used in combination (for example, may be used as a kit in combination) with one or more, preferably one to three, and more preferably one or two additional glaucoma or ocular hypertension therapeutic agents, or may contain an additional active ingredient. There is no particular limitation on the additional glaucoma or ocular hypertension therapeutic agents. Specifically, commercially available or developing glaucoma or ocular hypertension therapeutic agents and the like are preferable, commercially available glaucoma or ocular hypertension therapeutic agents and the like are more preferable, and commercially available glaucoma or ocular hypertension therapeutic agents having a different mechanism of action from that of the present compound are particularly preferable. More specific examples include glaucoma or ocular hypertension therapeutic agents containing, as active ingredients, non-selective sympathomimetics, $\alpha_2$-receptor agonists, $\alpha_1$-receptor blockers, $\beta$-receptor blockers, parasympathomimetics, carbonic anhydrase inhibitors, prostaglandins, Rho kinase inhibitors, and the like. Specific examples of the additional active ingredient include non-selective sympathomimetics, $\alpha_2$-receptor agonists, $\alpha_1$-receptor blockers, $\beta$-receptor blockers, parasympathomimetics, carbonic anhydrase inhibitors, prostaglandins, Rho kinase inhibitors, and the like. Note that, when the pharmaceutical preparation of the present invention is used in combination with the additional glaucoma or ocular hypertension therapeutic agent or contains the additional active ingredient, the "rate of decrease between pre-treatment intraocular pressure and post-treatment intraocular pressure (rate of decrease in intraocular pressure) attributed to the pharmaceutical preparation of the present invention" and the "width of decrease (variation of intraocular pressure)" described above mean a portion excluding the efficacies of the additional glaucoma or ocular hypertension therapeutic agent or the additional active ingredient.

Specific examples of the non-selective sympathomimetics include dipivefrine, specific examples of the $\alpha_2$-receptor agonists include brimonidine and apraclonidine, specific examples of the $\alpha_1$-receptor blockers include bunazosin, specific examples of the $\beta$-receptor blockers include timolol, befunolol, carteolol, nipradilol, betaxolol, levobunolol, and metipranolol, specific examples of the parasympathomimetics include pilocarpine, specific examples of the carbonic anhydrase inhibitors include dorzolamide, brinzolamide, and acetazolamide, specific examples of the prostaglandins include isopropyl unoprostone, bimatoprost, and travoprost, and specific examples of Rho kinase inhibitors include fasudil.

[Route of Administration]

The pharmaceutical preparation of the present invention can be administered orally or parenterally, such as ophthalmic administration, intravitreal administration, conjunctival sac administration, intracameral administration, subconjunctival administration, subtenon sac administration, or punctal plug administration. The dosage form of the pharmaceutical preparation of the present invention includes eye drops, ophthalmic ointments, injections, punctal plugs, tablets, capsules, granules, powders, and the like, and eye drops, ophthalmic injections, and punctal plugs are particularly preferable. The ophthalmic injections include injections for intravitreal administration, intracameral administration, conjunctival sac administration, intracameral administration, subconjunctival administration, or subtenon administration. The dosage form of the pharmaceutical preparation of the present invention can be produced according to conventional methods in the technical field of drugs. In addition to the above-described additives, oral preparations such as tablets, capsules, granules, and powders can be prepared by using, as necessary, bulking agents such as lactose, crystalline cellulose, starch, and vegetable oil, lubricants such as magnesium stearate and talc, binders such as hydroxypropylcellulose and polyvinylpyrrolidone, disintegrators such as carboxymethylcellulose calcium and low-substituted hydroxypropyl methylcellulose, coating agents such as hydroxypropyl methylcellulose, macrogol, and silicone resin, filmed medicines such as gelatin coating, and the like.

The pharmaceutical preparation of the present invention can be stored in containers made of various materials. For example, containers made of polyethylene, polypropylene, and the like can be used, and in the case of use as an eye drop, the pharmaceutical preparation of the present invention is preferably stored in a polyethylene container from the viewpoint of e.g. ease of instillation (hardness of the container) and stability of the present compound.

[Dosage and Administration]

The dosage and administration of the pharmaceutical preparation of the present invention are not particularly limited as long as they are dosage and administration sufficient to produce the desired efficacy, and can be appropriately selected according to the symptoms of the disease, the age and weight of the patient, the dosage form of the pharmaceutical preparation, and the like.

Specifically, in the case of an eye drop, one to five drops, preferably one to three drops, more preferably one or two drops, and particularly preferably one drop per dose may be ophthalmically administered one to four times a day, preferably one to three times a day, more preferably once or twice a day, and particularly once a day with a frequency of every day to every week. It is preferable that the eye drop be instilled at one drop once a day every day. Here, one drop is usually about 0.01 to about 0.1 mL, preferably about 0.015 to about 0.07 mL, more preferably about 0.02 to about 0.05 mL, and particularly preferably about 0.03 mL.

In the case of an ophthalmic injection, it is preferably 1 to 1000 µL, more preferably 5 to 700 µL, further preferably 10 to 500 µL, and most preferably 20 to 300 µL at a time. The dose of the drug is preferably 0.0001 to 30000 µg/eye, more preferably 0.0005 to 10000 µg/eye, and most preferably 0.001 to 5000 µg/eye. When the pharmaceutical preparation of the present invention is continuously administered as an ophthalmic injection, there is no particular limitation on the administration interval as long as it is sufficient to produce the desired efficacy. However, the administration interval is preferably once a week to once every three years, the administration interval is more preferably once a week, once every two weeks, once a month, once every two months, once every three months, once every four months, once every five months, once every six months, once a year, once every two years, or once every three years, and most preferably once every two months, once every three months, once every four months, once every five months or once every six months. In addition, the administration interval can be appropriately changed.

In the case of an oral preparation, it can be administered at 0.01 to 5000 mg, and preferably 0.1 to 1000 mg per day in one to several times separately (two to five times, preferably two or three times).

[Administration Method]

The pharmaceutical preparation of the present invention is subsequently administered when sufficient efficacies are not obtained or are not expected to be obtained by treatment or prevention with the above-described other glaucoma or ocular hypertension therapeutic agents. Specifically, the method of administering the pharmaceutical preparation of the present invention includes (1) a first treatment step of treating or preventing glaucoma or ocular hypertension with the above-described other active ingredients other than omidenepag, an ester thereof, or a salt thereof, (2) an optional step of judging whether the first treatment step is inadequate in treatment or inadequate in preventive effect, and (3) a second treatment step of, following the first treatment step, treating or preventing glaucoma or ocular hypertension by administering a pharmaceutical preparation containing omidenepag, an ester thereof, or a salt thereof as an active ingredient.

When the pharmaceutical preparation of the present invention is administered to a patient based on the administration method as described above, the pharmaceutical preparation of the present invention additionally provides an intraocular pressure lowering efficacy and the like, and further makes it possible to treat or prevent glaucoma or ocular hypertension regardless of the efficacies of treatment or prevention with above-described other active ingredients, or when the efficacies are inadequate.

The above administration method is described more specifically. First, the other glaucoma or ocular hypertension therapeutic agents (other active ingredients) other than the omidenepag, the ester thereof, or the salt thereof of the present invention are administered to treat or prevent glaucoma or ocular hypertension. Thereafter, when the other active ingredients are expected to have an inadequate therapeutic effect or inadequate preventive effect, they are judged as "glaucoma resistant to treatment of glaucoma with the other active ingredients" or "ocular hypertension resistant to treatment of ocular hypertension with the other active ingredients." Subsequently, the omidenepag, the ester thereof, or the salt thereof of the present invention is administered. Here, the case of being "expected to have an inadequate therapeutic effect or inadequate preventive effect" includes the case of approximately the rate of decrease in intraocular pressure and the width of decrease in intraocular pressure for the above-described "patients who cannot benefit from sufficient efficacies by treatment with other glaucoma or ocular hypertension therapeutic agents" as well as the case where the absolute value of intraocular pressure is still high enough to be judged as glaucoma or ocular hypertension, for example, 22 mmHg or more, preferably 21.5 mmHg or more, more preferably 21 mmHg or more, further preferably 20.5 mmHg or more, and particularly preferably 20 mmHg or more. If the glaucoma or ocular hypertension still does not cure or the potential risk of recurrence remains even after administration of the above-described other active ingredients, it is appropriate to use the pharmaceutical preparation of the present invention as a secondary administration means. As described above, in the case where the treatment and the like of glaucoma or ocular hypertension with the above-described other active ingredients such as latanoprost are inadequate and even in the case where the other active ingredients are considered having completed treatment or prevention sufficiently based on the conventional knowledge, the pharmaceutical preparation of the present invention provides unexpected operations and efficacies that treatment or prevention can be completed further, and solves a problem different from the conventional one.

For example, take latanoprost as the other active ingredient. In the case where glaucoma or ocular hypertension is treated and prevented with latanoprost and then further lowering of intraocular pressure is necessary, or in the case where a rebound in intraocular pressure takes place or is expected after treatment or prevention with latanoprost, the pharmaceutical preparation of the present invention can be expected to have an effect on the request for lowering the intraocular pressure or on the prevention of rebound of the intraocular pressure.

Examples relating to Preparation Examples and clinical test results of the present invention are presented below. Note that these examples are for better understanding of the present invention, and do not limit the scope of the present invention.

EXAMPLES

Preparation Example

The omidenepag, the ester thereof, or the salt thereof of the present invention can be used for the production of the pharmaceutical preparation as described above. Hereinafter, representative preparation examples of the pharmaceutical preparation of the present invention are presented. Note that, in the following preparation examples, the amount of each of the ingredients is the content in 100 mL of the preparation.

Preparation Example 1

Eye Drop 1 (in an amount of 100 mL)
Omidenepag Isopropyl 0.002 g
Boric Acid 0.2 g
Glycerin 2.0 g
Polysorbate 80 0.5 g
Disodium Edetate 0.05 g
Benzalkonium Chloride 0.005 g
Dilute Hydrochloric Acid quantum sufficit
Sodium Hydroxide quantum sufficit
Purified Water quantum sufficit Preparation Example 2

Eye Drop 2 (in an amount of 100 mL)
Omidenepag Isopropyl 0.002 g
Sodium Dihydrogen Phosphate 0.2 g
Glycerin 2.0 g
Vitamin E TPGS 0.8 g
Disodium Edetate 0.05 g
Benzalkonium Chloride 0.005 g
Dilute Hydrochloric Acid quantum sufficit
Sodium Hydroxide quantum sufficit
Purified Water quantum sufficit Preparation Example 3

Eye Drop 3 (in an amount of 100 mL)
Omidenepag Isopropyl 0.002 g
Trisodium Citrate 0.2 g
Glycerin 2.0 g
Polyoxyethylene Hydrogenated Castor Oil 60 0.3 g
Disodium Edetate 0.05 g
Benzalkonium Chloride 0.005 g
Dilute Hydrochloric Acid quantum sufficit
Sodium Hydroxide quantum sufficit
Purified Water quantum sufficit Preparation Example 4

Injection 1 (in an amount of 100 mL)
Omidenepag 0.003 g
PEG 400 quantum sufficit Preparation Example 5

Injection 2 (in an amount of 100 mL)
Omidenepag 0.0003 g
PEG 400 quantum sufficit Note that, in Preparation Examples 1 to 5, the desired pharmaceutical preparation can be obtained by appropriately adjusting the type and/or amount blended of omidenepag and/or additive. In particular, the desired pharmaceutical preparation can be obtained by setting the amount blended of omidenepag in Preparation Examples 1 to 5 to 0.001 g, 0.0011 g, 0.0012 g, 0.0013 g, 0.0014 g, 0.0015 g, 0.0016 g, 0.0017 g, 0.0018 g, 0.0019 g, 0.0021 g, 0.0022 g, 0.0023 g, 0.0024 g, 0.0025 g, 0.0026 g, 0.0027 g, 0.0028 g, 0.0029 g, or 0.003 g.

[Clinical Test]

Examination was conducted on the efficacy of omidenepag isopropyl on patients with inadequate efficacies of other glaucoma or ocular hypertension therapeutic agents.

1. Preparation of Eye Drop

Omidenepag isopropyl, polyoxyl 35 castor oil, glycerin, citric acid, sodium citrate, sodium edetate, and benzalkonium chloride were dissolved into purified water to adjust the pH. Thereafter, purified water was added to adjust the total volume, thereby preparing a 0.002% (w/v) omidenepag isopropyl eye drop A.

2. Test Method

Patients with primary open angle glaucoma or ocular hypertension were subjected to a washout period of 1 to 4 weeks, and then received a binocular instillation of 0.005% latanoprost ophthalmic solution in an amount of 1 drop once a day for 8 weeks as an induction phase (week −8 to baseline). The patients with primary open angle glaucoma (21 humans) or ocular hypertension (5 humans) resistant to treatment with latanoprost ophthalmic solution, whose rate of decrease in intraocular pressure from the start of instillation was 15% or less at the end of the induction phase, entered the treatment phase (baseline to week 4), and received a binocular instillation of the above-described 0.002% (w/v) omidenepag isopropyl eye drop A in an amount of 1 drop (about 0.03 mL) once a day for 4 weeks every day.

3. Test Results and Discussion

FIG. 1 presents the results.

The variation of intraocular pressure (mean±standard error) 4 weeks after instillation, which is the point in time (week 4) at the end of the treatment phase, from the point in time (baseline) at switching from the 0.005% latanoprost ophthalmic solution in the induction phase to the 0.002% (w/v) omidenepag isopropyl eye drop in the treatment phase was −2.99±0.43 mmHg. Thus, a statistically significant decrease in intraocular pressure (P<0.0001) was observed. Also, the rate of decrease in intraocular pressure (intraocular pressure decrease rate) at the end of the treatment phase (week 4) relative to the intraocular pressure at the baseline was 13.2%. This has made it clear that omidenepag isopropyl lowers intraocular pressure to a greater extent than latanoprost instillation in patients resistant to latanoprost treatment.

It has been found from the above that omidenepag, an ester thereof, or a salt thereof has an excellent intraocular pressure lowering efficacy on patients with inadequate efficacies of other glaucoma or ocular hypertension therapeutic agents.

What is claimed is:

1. A method of treating glaucoma or ocular hypertension, comprising: administering to a patient a pharmaceutical preparation containing omidenepag, an ester thereof, or a salt thereof as an active ingredient, wherein the patient is a patient with inadequate efficacies of latanoprost such that, when subjected to treatment with latanoprost, a) a width of decrease between pre-treatment intraocular pressure and post-treatment intraocular pressure is 4.5 mmHg or less, or b) a rate of decrease between pre-treatment intraocular pressure and post-treatment intraocular pressure is 18% or less.

2. The method according to claim 1, wherein the treatment of glaucoma or ocular hypertension includes treating glaucoma or ocular hypertension with latanoprost and then further treating glaucoma or ocular hypertension by lowering intraocular pressure with the active ingredient.

3. The method according to claim 1, wherein a content of the omidenepag, the ester thereof, or the salt thereof in the pharmaceutical preparation is 0.001 to 0.003% (w/v).

4. The method according to claim 1, wherein a content of the omidenepag, the ester thereof, or the salt thereof in the pharmaceutical preparation is 0.002% (w/v).

5. The method according to claim 1, wherein the omidenepag, the ester thereof, or the salt thereof is omidenepag isopropyl.

6. The method according to claim 1, wherein the administration is ophthalmic administration.

7. A method of treating glaucoma or ocular hypertension, comprising: administering to a patient a pharmaceutical preparation containing omidenepag, an ester thereof, or a salt thereof as an active ingredient, wherein the glaucoma is glaucoma resistant to treatment of glaucoma with latanoprost, and the ocular hypertension is ocular hypertension resistant to treatment of ocular hypertension with latanoprost such that, when subjected to treatment with latanoprost, a) a width of decrease between pre-treatment intraocular pressure and post-treatment intraocular pressure is 4.5 mmHg or less, or b) a rate of decrease between pre-treatment intraocular pressure and post-treatment intraocular pressure is 18% or less.

8. A method of treating glaucoma or ocular hypertension including administering to a patient a pharmaceutical preparation containing omidenepag, an ester thereof, or a salt thereof as an active ingredient, the method comprising the following steps:
(1) a first treatment step of administering to a patient latanoprost, or a salt thereof;
(2) a step of judging whether the first treatment step is inadequate in treatment such that, a) a width of decrease between pre-treatment intraocular pressure and post-treatment intraocular pressure in the first treatment is 4.5 mmHg or less, or b) a rate of decrease between pre-treatment intraocular pressure and post-treatment intraocular pressure is 18% or less; and
(3) a second treatment step of further administering to a patient a pharmaceutical preparation containing omidenepag, an ester thereof, or a salt thereof as an active ingredient when the first treatment step is inadequate in terms of a) or b) of the step (2).

9. A method of treating glaucoma or ocular hypertension, comprising:
confirming that a patient is a patient with inadequate efficacies of latanoprost such that, when subjected to treatment with latanoprost, a) a width of decrease between pre-treatment intraocular pressure and post-treatment intraocular pressure is 4.5 mmHg or less, or b) a rate of decrease between pre-treatment intraocular pressure and post-treatment intraocular pressure is 18% or less, and then
administering to the patient a pharmaceutical preparation containing omidenepag, an ester thereof, or a salt thereof as an active ingredient.

10. A method of treating glaucoma or ocular hypertension, comprising:
confirming that the glaucoma is glaucoma resistant to treatment of glaucoma with latanoprost, and that the ocular hypertension is ocular hypertension resistant to treatment of latanoprost, such that, when subjected to treatment with latanoprost, a) a width of decrease between pre-treatment intraocular pressure and post-treatment intraocular pressure is 4.5 mmHg or less, or b) a rate of decrease between pre-treatment intraocular pressure and post-treatment intraocular pressure is 18% or less, and then
administering to a patient a pharmaceutical preparation containing omidenepag, an ester thereof, or a salt thereof as an active ingredient.

* * * * *